United States Patent [19]

Theeuwes

[11] 4,036,228
[45] July 19, 1977

[54] OSMOTIC DISPENSER WITH GAS GENERATING MEANS

[75] Inventor: Felix Theeuwes, Los Altos, Calif.

[73] Assignee: Alza Corporation, Palo Alto, Calif.

[21] Appl. No.: 612,465

[22] Filed: Sept. 11, 1975

[51] Int. Cl.² .......................................... A61M 31/00
[52] U.S. Cl. .................................. 128/260; 128/225; 424/14
[58] Field of Search ............... 128/260, 225, 261, 270, 128/213

[56] References Cited

U.S. PATENT DOCUMENTS

| | | | |
|---|---|---|---|
| 536,155 | 3/1895 | Noyes | 424/16 |
| 1,356,544 | 10/1920 | Miller | 424/14 |
| 1,707,762 | 4/1929 | Homan | 424/14 X |
| 3,604,417 | 9/1971 | Stolzenberg et al. | 128/225 |
| 3,756,236 | 9/1973 | Murray et al. | 128/225 |
| 3,916,899 | 11/1975 | Theeuwes et al. | 128/260 |

*Primary Examiner*—Lawrence Charles
*Attorney, Agent, or Firm*—Paul L. Sabatine; Thomas E. Ciotti; Edward L. Mandell

[57] ABSTRACT

An osmotic device for delivering an active agent is disclosed. The device is comprised of a wall surrounding a compartment and has a passageway through the wall for dispensing the agent. The wall is formed of a material permeable to an external fluid and substantially impermeable to agent and a gas generating means. The compartment is comprised of an active agent and a gas generating means that either exhibits an osmotic pressure gradient against the external fluid, or the means is mixed with an osmotically effective compound that exhibits an osmotic pressure gradient against the fluid. Agent is released by fluid being imbibed through the wall into the compartment at a rate controlled by the permeability of the wall and the osmotic pressure gradient across the wall, which fluid wets the means causing it to react and produce an effervescent solution containing agent that is dispensed under pressure through the passageway to the exterior of the device.

24 Claims, 5 Drawing Figures

OSMOTIC DISPENSER WITH GAS GENERATING MEANS

FIELD OF THE INVENTION

This invention pertains to an osmotic device for delivering an active agent. More particularly, the invention relates to an osmotic device that uses a gas generating means such as an effervescent couple to deliver an active agent at a controlled and continuous rate over a prolonged period of time from the device to an environment of use.

BACKGROUND OF THE INVENTION

Osmotic devices for delivering an active agent to an environment of use are known to the prior art in U.S. Pat. Nos. 3,760,984 and 3,845,770. The devices disclosed in these patents comprise a wall formed of a material permeable to an external fluid and impermeable to agent with the wall surrounding a compartment containing an agent and having a passageway for dispensing the agent. Generally, these devices are remarkably effective for delivering an agent that is either soluble in the fluid and exhibits an osmotic pressure gradient across the wall against the fluid or for delivering an agent that has limited solubility in the fluid and is admixed with an osmotically effective compound soluble in the fluid that exhibits an osmotic pressure gradient against the fluid. The devices release agent by fluid being continuously imbibed through the wall into the compartment at a rate determined by the permeability of the wall and the osmotic pressure gradient across the wall to correspondingly continuously produce a solution of soluble agent or a solution of soluble compound containing agent which solution in either operation is dispensed from the device. While the above devices represent a significant and pioneer advancement in the art, there is an occasional application for dispensing an agent where a larger volume flow could be used than can be obtained with an osmotic system. For example, if the agent is practically insoluble in the external fluid, a larger volume of flow could advantageously be used for substantially preventing the agent from settling in the compartment and for dispensing agent from the device.

OBJECTS OF THE INVENTION

Accordingly, it is an immediate object of this invention to provide an osmotic device that comprises a means for improving the dispensing of an active agent from the device.

Another object of the invention is to provide an osmotic device for dispensing an agent that has limited solubility in a fluid that enters the device with the device having a means for dispensing the agent in a predetermined amount at a controlled and continuous rate to the environment of use.

Another object of the invention is to provide an osmotic device for increasing the utility of short acting drugs and long acting drugs that, because of their inherent physical and chemical properties, are difficult to dispense at a controlled and continuous rate, and which drugs can be dispensed with the device of the invention at a controlled and continuous rate to perform a satisfactory therapeutic use over a prolonged period of time.

Yet another object of the invention is to provide an osmotic device that is designed with a minimum number of parts and has a large volume flow of medium that provides shearing action for delivering an agent by volume displacement delivery from the device.

Yet still another object of the invention is to provide an osmotic device for delivering a drug that is difficult to deliver and requires multiple deliveries to obtain a prolonged action which device can deliver the drug for a prolonged period of time and concomitantly eliminate the necessity for taking multiple doses of the drug.

Still another object of the invention is to provide an osmotic device that can deliver all kinds of drugs and has an economic advantage for the user by keeping to a minimum the number of doses to be administered and reducing missed doses because of forgetfulness.

Still a further object of the invention is to provide an osmotic dispensing system that can administer a complete pharmaceutical regimen to a human for a particular time period, the use of which requires intervention only for initiation and termination of the regimen.

Other objects, features, and advantages of the invention will be more apparent to those skilled in the art from the detailed description of this specification, taken in conjunction with the drawings and the accompanying claims.

SUMMARY OF THE INVENTION

This invention concerns an osmotic device useful for dispensing an agent, having in one embodiment a limited solubility in an aqueous-type medium, to an environment of use. The device is comprised of a wall surrounding a compartment and having a passageway communicating with the compartment and the exterior of the device. The wall is formed of a semipermeable material and the compartment contains the agent, a gas generating means such as an effervescent couple and it can also contain an osmotically effective compound, a surfactant and a foaming agent. Agent is released by fluid being imbibed through the wall wetting the means or couple and causing it to generate a large volume of agent-carrying medium for dispensing the agent by volume displacement from the device.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by like numbers. The terms appearing earlier in the specification and the description of the drawings, as well as embodiments thereof, are further described elsewhere in the disclosure.

DETAILED DESCRIPTION OF THE DRAWINGS

Figure 1A:
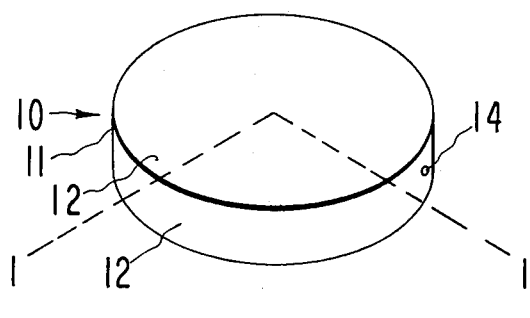
FIG. 1A is a perspective view of an osmotic device illustrating the top and side surfaces and a passageway in the side surface of the device.
Figure 1B:
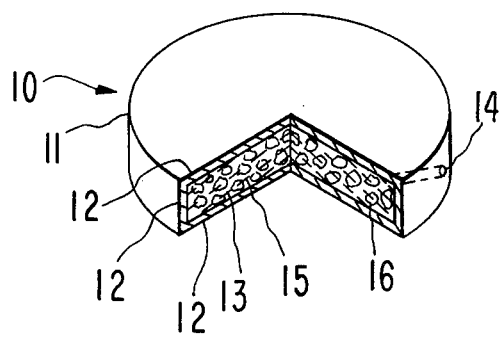
FIG. 1B is a view through 1—1 of FIG. 1A depicting the device in opened-section for illustrating the structure of the walls and the interior compartment of the device.

Turning now to the drawings in detail, one device for dispensing an agent is indicated in FIGS. 1A and 1B, considered together, by the number 10. Device 10 is comprised of a body 11 having a wall 12 that surrounds a compartment 13, seen in FIG. 1B in opened-section along lines 1—1 of FIG. 1A, and a passageway 14 in wall 12 that communicates with compartment 13 and the exterior of device 10. Compartment 13 is comprised of an agent 15 having various degrees of solubility in an external fluid that enters the compartment, for example soluble to very soluble, and in a preferred embodiment, agent 15 has limited solubility or is substantially practically insoluble in the external fluid. Agent 15, when possessed with the latter two solubilities, is mixed with a gas generating means 16, such as an effervescent couple that is soluble in the fluid and exhibits an osmotic pressure gradient across wall 12, or means 16 has limited solubility in the fluid and is mixed with an osmotically effective compound that exhibits an osmotic pressure gradient against the fluid. Agent 15 when soluble, can exhibit an osmotic pressure gradient and be mixed with a means that exhibits a small pressure gradient. Compartment 13 also can contain a surfactant for wetting the active agent and a foaming agent that provides a stable structure for carrying the active agent from the device. The gas generating means provides gas and shearing action for enhancing by volume displacement, active agent from the device.

Wall 12 of device 10 is formed in total or in at least a part of a semipermeable material that is permeable to an external fluid and substantially impermeable to agent 15, means 16, and other compounds housed in compartment 13. When wall 12 is formed in part of a semipermeable material, the remainder of 12 is formed of a material that is substantially impermeable to fluid and to the passage of agent 15, means 16, and other compounds housed in compartment 13. A detailed description of semipermeable materials, gas generating means and effervescent couples, and other compounds appear later in the specification. In operation in the environment of use, when compartment 13 contains an agent 15 having limited solubility in the fluid and a gas generating means 16, such as an effervescent couple that exhibits an osmotic pressure gradient, device 10 releases agent 15 by fluid being imbibed into compartment 13 in a tendency towards osmotic equilibrium at a rate controlled by the permeability of wall 12 and the osmotic pressure gradient across the wall to continuously wet and dissolve means 16 causing it to react and produce a large effervescent volume that, by volume displacement, carries agent 15 homogenously and heterogenously dispersed therein through passageway 16 from device 10. When, in a presently preferred embodiment, compartment 13 contains a foaming agent, a large volume of foam is generated in compartment 13 that carries agent 15 from device 10 with agent 15 being dispensed substantially free of precipitation. Device 10 of FIGS. 1A and 1B can be sized and adapted for use as a buccal tablet, for oral administration of a medicine to animals, including cattle, sheep, goats, pigs and horses, and for human use. Device 10 also can be adapted for releasing an active agent such as a fertilizer in plowed fields, and for use in like environments.

Figure 2A:
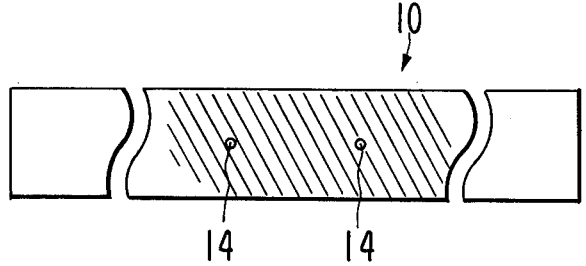
FIG. 2A is a fragmentary view of another embodiment illustrating a rectangular-shaped device having two passageways for releasing an active agent.
Figure 2B:
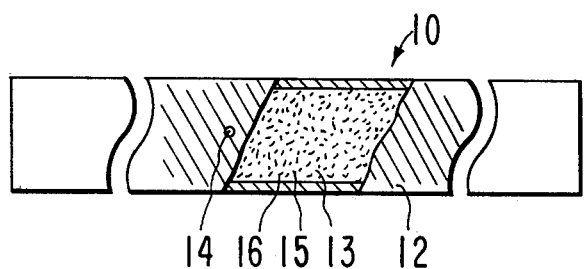
FIG. 2B is a further view of 2A as seen in opened-section with a portion of the top wall removed for illustrating the interior of the device and its contents.

FIG. 2A and accompanying FIG. 2B, illustrated with a portion of its wall removed, represent another device 10 manufactured according to the invention. Device 10 is comprised of a semipermeable wall 12 surrounding a compartment 13 having two passageways 14 through wall 12 for releasing agent 15. Passageways 14 can have the same or different sizes so long as the total opened area lets device 10 operate as an osmotic device. Compartment 13 contains an agent 15, a gas generating means 16 such as an effervescent couple and preferably, as in FIGS. 2A and 2B, a foaming agent and a surfactant. Device 10 operates like device 10 of FIGS. 1A and 1B, that is, on exposure of device 10 to an external fluid, the fluid is imbibed into device 10 and causes the means to produce gas that in the presence of the foaming agent will build a foam to carry a substantially insoluble agent 15 from device 10. The improved advantage of this device is that imbibed fluid produces a gas volume of large or amplified magnitude creating an outflow volume which is larger than the influx volume. The volume amplification also is beneficial in that it increases the shear in compartment 13 and promotes mixing of agent 15 with the foam for a better release of agent 15 at a controlled and continuous rate from device 10. Device 10 can be sized and adapted for many uses, such as for topical release of an agent, for releasing a steroid of limited solubility, for releasing a nutrient in an aquarium, and for like applications.

Figure 3:
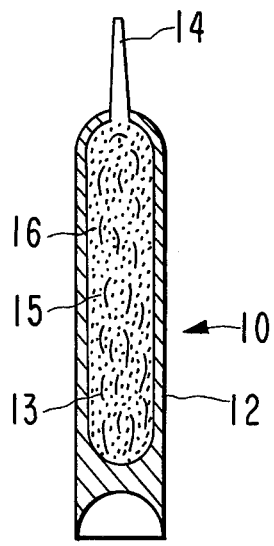
FIG. 3 is a longitudinal sectional view of another embodiment consisting of a dispensing ampoule having a tapered outlet for releasing agent.

FIG. 3 represents another device 10 fabricated according to the invention. Device 10 is shaped like a dispensing cartridge with a tapered osmotic passageway 14 for dispensing an agent 15 under gas or effervescent pressure to an environment of use. The numbered parts in FIG. 3 and the operation of the cartridge correspond to the numbered parts and the operation for device 10 as defined in the above figures. Device 10 of FIG. 3 can be used to dispense a medicinal agent 15 into a body opening such as the mouth, the anus, or the vagina, and for dispensing a drug into an eye or into an ear.

DETAILED DESCRIPTION OF THE INVENTION

In attaining the objects, features and advantages of the invention, it has now been found that semipermeable materials suitable for forming the wall(s) of the device are materials that can form wall membranes and do not adversely affect the device, the agent, an animal host or the environment of use. The semipermeable materials are permeable to an external fluid, including aqueous and physiological fluids, substantially impermeable to agent, gas generating means, effervescent couple and other compounds in the compartment, and they are of synthetic or naturally occuring origin. Typical semipermeable membranes include cellulose acetate, cellulose triacetate, agar acetate, amylose triacetate, beta glucan acetate, beta glucan triacetate, acetaldehyde dimethylacetate, and cellulose acetate ethyl carbamate. Exemplary materials also include materials that erode after the device has released agent in the environment of use. Other semipermeable membranes as disclosed in U.S. Pat. Nos. 3,760,984 and 3,845,770.

The gas generating means suitable for the purpose of the invention is, in a presently preferred embodiment, an effervescent couple or composition. The effervescent couple comprises at least one preferably solid acidic material and a preferably solid basic material that dissolve and react in an aqueous fluid that enters the device to produce carbon dioxide effervescent that leads to volume displacement of agent from the device. The couple is present in the compartment mixed with the agent in the powder, crystalline, granular, or layered form. The acids that can be used include pharmaceutically acceptable organic acids such as malic, fumaric, tartaric, itaconic, maleic, citric, adipic, succinic and mesaconic, mixtures thereof, and the corresponding anhydride such as itaconic anhydride and citriconic anhydride. Also, inorganic acids can be used such as sulfamic or phosphoric, and the acid disclosed in U.S. Pat. No. 3,325,357. Acid salts such as the salts of organic food can be used including monosodium citrate, potassium acid tartrate and potassium bitartrate. The basic compounds include preferably the pharmaceutically acceptable metal carbonate and bicarbonate salts such as alkali metal carbonates and bicarbonates or alkaline earth carbonates and bicarbonates and mixtures thereof. Exemplary materials include the alkali metals lithium, sodium, and potassium carbonate and bicarbonate, and the alkaline earth compounds magnesium and calcium carbonate or bicarbonate. Also useful are ammonium carbonate, ammonium bicarbonate, and ammonium sesquecarbonate. The combination of certain of these acids and bases results in a more rapid gas production or effervescence when contacted by water than do other of the above-listed groups. In particular, either citric acid or a mixture of citric acid and tartaric acid and sodium bicarbonate give a rapid gaseous reaction that is useful for quick release from the device. It will be understood the amount of acidic and basic materials in a couple can vary over a wide range to satisfy the amount of effervescent needed to dispense an agent. The essentially anhydrous or dry couple is preferably substantially stoichiometrically balanced to produce a combination that generates carbon dioxide. Also, the acid and base materials can be used in any convenient proportion between 1 to 200 parts and 200 to 1 parts on a weight basis to produce the desired results.

Additionally, the gas generating means includes effervescent couples which form a salt and can hydrate and store up to several moles of water per mole of salt. For these couples, the rate at which gas is produced and agent dispensed from the device is controlled by the influx of water imbibed into the system. Control is effected by hydration of the salt that quenchs the chain reaction of gas production caused by the acid base reaction. Further, a water scavenging process can be added to the compartment to fulfill the same function. The gas generating means also can consist of a single gas producing agent, such as calcium carbide, that evolves a gas on exposure to water. The latter means is particularly useful for non-therapeutic applications.

The surfactants useful for the purpose of the invention include those having wetting, solubilizing and foaming properties and aid in increasing the volume of medium generated in the compartment for the volume displacement of agent from the device. The surfactants can be cationic, anionic or nonionic. Exemplary cationic surfactants include, lauryldimethylbenzylammonium chloride, p-diisobutylphenoxyethoxyethyl-dimethylbenzylammonium chloride, alkyldimethylbenzylammonium chloride, laurylisoquinolinium bromide, cetylethyldimethylammonium bromide, stearyldimethylbenzylammonium chloride, N-soya-N-ethyl-morpholinium-ethosulphate, N(acyl-colamino-formyl-methyl)pyridinium chloride, a mixture comprising alkyl($C_9H_{19}$ to $C_{15}H_{31}$)tolylmethyltrimethylammonium chloride and laurylisoquinolinium bromide, cocoamidoalkyl betaine, and N-lauryl-myristyl$\beta$-aminopropionic acid. Exemplary anionic surfactants include linear alkylaryl sulfonates prepared by Friedel-Crafts reaction of an olefin and benzene wherein the olefin has from 10 to 18 carbon atoms, and the alkali metal salts thereof, and other anionic surfactants such as alkylaryl sulphonate, capryl imidazoline derivatives, dioctylester of sodium sulphosuccinic acid, sodium lauryl sulfate, sodium salt of alkylated aryl polyether sulphate, triethanolamine salt of lauryl sulphate, triethanolamine salt of alkylaryl sulphonate, and mixtures thereof. Exemplary nonionic surfactants include alkylated aryl polyether alcohol, polyethylene glycol tertdodecyl thioether, fatty acid amide condensates, aromatic polyglycol ether condensates, secondary amide of lauric acid, fatty acid alkanolamine condensates, sorbitan monolaurate, sorbitan monolaurate polyoxyethylene, sorbitan mono-oleate, sorbitan mono-oleate polyoxyethylene derivative, mannide mono-oleate polyoxyethylene laurylether, polyoxyethylene esters of mixed resins and fatty acids, and mixtures thereof, and surfactants generically including the condensation product of a linear aliphatic alcohol having from 8 to 22 carbon atoms in its aliphatic portion and an alkylene oxide wherein the oxide constitutes from about 55 to 80% by weight of the surfactant molecule. The amount of surface active agent used is an amount sufficient to achieve the intended result, normally, the amount will range from 0.01% to about 15% by weight, based on the total weight of all the compounds in the device. The surface active agents are commercially available and they are also known in *Solubilization By Surface-Active Agents*, by Elworthy, P. H., et al, 1968 published by Chapman and Hall Ltd., London; *Systemic Analysis of Surface-Active Agents*, by Rosen, Milton J., et al, 1972, published by Wiley-Interscience Inc., Sydney; *Encyclopedia of Polymer Science and Technology*, Vol. 13, pages 477 to 486, 1970, published by John Wiley & Sons Inc., New York; and U.S. Pat. Nos. 2,674,619, 3,340,309, 3,504,401, and 3,796,187. A number of surface active agents also are foam-formers and for those, a single surfactant can be used as a surfactant and as a foam-former. Representative foam-formers are set forth immediately below.

Exemplary foam-forming agents are those that produce a copious foam for volume displacement of agent when used in relatively small amounts, that produce a foam that is stable within a wide range of temperature, that produces a foam that does not collapse in the presence of other compounds, and produces a foam that is pharmaceutically acceptable when the device is used to dispense a drug, usually of limited solubility. Typical foam-formers are alkyl aryl sulphonates, sodium ammonium and alkanolamine ether sulphates such as monoethanolamine lauryl ether sulphate and dodecyl benzene sulphonate, a mixture consisting of laurylamido-propyl-N-dimethylamino acetic acid and stearylamin-dopropyl-N-dimethylamino acetic acid, a mixture consisting of monoethanolamine lauryl ether sulphate and methyl cellulose in a weight ratio of 3:1, a foaming surfactant consisting of sodium alkyl benzene sulphonate in combination with lauryl sulphate and sodium lauryl sulphoacetate. The amount of foam-forming agent used usually is about 0.01 to 15% by weight based on the total weight of the compounds in the device. Representative foam-formers and foam systems are described in *The Theory and Practice of Industrial Pharmacy*, by Lachman, L. et al, pages 618 to 621, 1970, published by Lea & Febiger, Philadelphia; and in *Cosmeticology*, by Harry, R. G., pages 243 to 250, 1973, published by Chemical Publishing Co. Inc., New York.

The osmotically effective compounds that can be used for the purpose of the invention include organic and inorganic compounds that exhibit an osmotic pressure gradient against an external fluid across the semipermeable wall of the device. Generally, the presence of an added compound in the device is superfluous as the gas generating means or at least one component of an effervescent couple, for example, sodium bicarbonate, will exhibit an osmotic pressure gradient. In those applications when the means exhibits a limited osmotic pressure gradient, an osmotically effective compound is homogenously or heterogenously mixed with the agent and the means in the device. In operation, these compounds attract fluid into the device wetting the means and causing it to react to produce an effervescent solution that concomitantly transports agent from the device. Osmotically effective compounds useful for the present purpose include inorganic and organic salts and polysaccharides such as magnesium sulfate, magnesium chloride, sodium chloride, lithium chloride, potassium sulfate, sodium carbonate, sodium sulfite, lithium sulfate, potassium chloride, calcium bicarbonate, sodium sulfate, calcium sulfate, potassium acid phosphate, calcium lactate, tartaric acid, lactose, fructose, mannitol, sorbitol, and mixtures thereof. The compound is initially present in excess and it can be in particle, crystal, pellet, or granule form. The osmotic pressure can be measured with a commercially available osmometer identified as Vapor Pressure Osmometer, Model 2B, available from Hewlett-Packard, Avondale, Penna.

The expression "active agent" as used herein broadly includes any compound, composition of matter or mixture thereof, that can be delivered from the device to produce a beneficial and useful result. The active agent includes pesticides, herbicides, germicides, biocides, algicides, rodenticides, fungicides, insecticides, anti-oxidants, plant growth promoters, plant growth inhibitors, preservatives, surfactants, disinfectants, sterilization agents, catalysts, chemical reactants, fermentation agents, foods, food supplements, nutrients, cosmetics, drugs, vitamins, air purifiers, micro-organism attenuators, and other agents that benefit the environment of use. The term "drug" includes any physiologically or pharmacologically active substance that produces a localized or systemic effect or effects in animals, including mammals, humans and primates, avians, domestic household, sport or farm animals such as sheep, goats, cattle, horses and pigs, for administering to laboratory animals such as mice, rats and guinea pigs, and to fishes, reptiles and zoo animals. The active agent can be soluble in an external fluid that enters the device, or in a presently preferred embodiment, the agent has a limited solubility or is substantially practically insoluble in the fluid. The terms "limited solubility" and "practically insoluble" generally mean the agent has a solubility of about less than 1% by weight in the fluid present in the device. The solubility of an agent in a fluid can be ascertained by using the procedure described in Remington's Pharmaceutical Sciences, Fourteenth Edition, pages 246 to 269, 1970, published by Mack Publishing Co., Easton Penna., and in U.S. Pat. No. 3,845,761. The active drug that can be used include gastrointestinal drugs such as bismuth subcarbonate that is practically insoluble in water, magnesium carbonate, also practically insoluble in water, antiemetics such as dimenhydrinate that is slightly soluble in water, coronary drugs such as pentaerythritol tetranitrate that is practically insoluble in water, digitaloid drugs such as digoxin that is substantially insoluble in water, centrally acting expectorants such as levopropoxyphene napsylate that is very slightly soluble in water, sympathomimetics such as levonordefrin practically insoluble in water, nylidrin hydrochloride having a solubility of 1 gm dissolving in 65 ml of water, quinidine sulfate having a solubility of 1 gm dissolving in 100 ml of water, norethindrone practically insoluble in water, norethynodrel very slightly soluble in water, diazepam 1 gm dissolves in 400 ml of water, anticholinesterases such as physostigmine salicylate having a solubility of 1 gm dissolving in 75 ml of water, antiadrenergic agents such as methyldopa sparingly soluble in water, antimuscarinic such as mepenzolate bromide having a solubility of 1 gm dissolving in 112 ml of water, carbonic anhydrase inhibitors such as acetazolamide, dichlorphenamide and methazolamide all very slightly soluble in water, and other drugs whose solubility is set forth in Remington's Pharmaceutical Science. Additionally, the device can be used for dispensing other drugs whose solubility is set forth in the Merck Index, Eighth Edition, 1968, published by Merck & Co., Inc., Rahway, New Jersey. Other drugs include tranquilizers such as chloropromazine, fluphenazine, reserpine, meprobamate and benzodiazepines such as chlordiazepoxide, muscle relaxants and antiparkinson agents such as mephenesin and levo-dopa, analgesics such as asprin, salicylamide, salicyclic acid, sodium salicylate, choline salicylate, acetaminophen, phenacetin, codeine and morphone; antimicrobials such as penicillin, tetracycline, oxytetracycline and chloramphenicol and sulfonamides, hormonal agents such as prednisolone, cortisone, cortisol, $17\beta$-estradiol, $\alpha$-estradiol, estriol, progesterone, 19-norpregn-4-ene-3,20-dione and 17-ethinyl-17-hydroxy-5(10)-estren-3-one with ethynylestradiol 3-methyl ether, hypoglycemic drugs such as insulin, isophane insulin, protamine zinc insulin suspension, tolbutamide, acetohexamide, tolazamide and chlorpropamide, nutritional agents such as ascorbic acid, niacin, nicotinamide, folic acid, choline, biotin, pantothenic acid, vitamin $B_{12}$, essential amino acids and essential fats, and electrolytes such as calcium gluconate, calcium lactate, potassium chloride, sodium chloride, potassium fluoride, ferrous compounds such as ferrous fumurate, ferrous citrate, ferrous carbonate, ferrous gluconate, ferrous sulfate, and sodium lactate.

The drug can also be in various forms, such as uncharged molecules, molecular complexes, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides which have solubility characteristics suitable for use herein can be used alone or mixed with other drugs. Also, a drug that is water soluble can be used in a form that is a water insoluble derivative thereof and on its release from the device is converted by enzymes, hydrolyzed by body pH or other metabolic processes to a biologically active form. The amount of agent, for example a drug, present in the device, generally is enough for a complete pharmaceutical dosage program. Generally, the device can house from 0.05 ng to 5 grams or more, with individual devices containing, for example, 1 mg, 5 mg, 250 mg, 500 mg, 1 g and 1.5 g.

The devices of the invention are manufactured by standard techniques. For example, in one embodiment, the agent is mixed with an effervescent couple by ballmilling, calendering, stirring and pressed into a preselected shape. The wall material forming the device can be applied by molding, spraying or dipping the pressed shape into the material. An osmotic passageway or aperture through the wall is made by mechanical drilling, laser drilling, punching or cutting with a die. The maximum and minimum dimensions for an osmotic passageway are disclosed in U.S. Pat. application Ser. No. 440,281 filed Feb. 7, 1974 and now U.S. Pat. No. 3,916,899. Other standard manufacturing procedures are described in *Modern Plastics Encyclopedia*, Vol. 46, pages 62 to 70, 1969; in *Remington's Pharmaceutical Science*, Fourteenth Edition, pages 1649 to 1968, 1970, published by Mack Publishing Co., Easton, Penna.; in *The Theory and Practice of Industrial Pharmacy*, by Lachman, et al, pages 197 to 225, 1970, published by Lea & Febiger, Philadelphia, Penna.; and in U.S. Pat. No. 3,845,770.

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic device comprised of an effervescent couple and acetylsalicylic acid is prepared by blending the components, in the following weight ratios:

| | |
|---|---|
| Acetylsalicylic acid | 10 |
| Citric acid | 25 |
| Sodium bicarbonate | 45 |
| Monocalcium phosphate dibasic | 0.125 |

The ingredients are weighed and mixed at 70° F (21° C) and at a relative humidity of between 10° and 15°. The ingredients are blended and mixed for 30 minutes in a commercially available mixer and then fed into a tablet press and pressed at 5 to 6 tons pressure. Next, the compressed tablet is coated with cellulose acetate commercially available as E-320 from Eastman Kodak by using an air suspension technique. A 5% polymer solution in dioxane is used to produce a coating of about 10 mils thick. A number of devices are made using this procedure and an osmotic passageway is placed in each by mechanical drilling with the diameter of the passageway ranging from 3.9 to 11.0 mils. The device in an aqueous environment imbibes fluid to the compartment causing the couple to generate an effervescent solution that dispenses acetylsalicylic acid in suspension from the device.

EXAMPLE 2

An oral, osmotic device that contains a composition which effervesces and produces a clear potable solution when the device imbibes water in the environment of use, is manufactured by following the procedure of Example 1. All conditions are as previously set forth except that the ingredients of this example are expressed in weight ratios and the device is useful in potassium replacement therapy. The ingredients are as follows:

| | |
|---|---|
| Potassium bicarbonate | 0.64 |
| Potassium chloride | 0.425 |
| Citric acid | 0.25 |
| Sucrose | 0.610 |

EXAMPLE 3

An osmotic device that effervesces and produces a foam is illustrated by a composition comprised of the following ingredients expressed in weight percent:

| | |
|---|---|
| Active agent | 30.00 |
| Myristic acid | 1.49 |
| Stearic acid | 1.60 |
| Cetyl alcohol | 0.50 |
| Lanolin | 0.20 |
| Isopropyl myristate | 1.33 |
| Triethanolamine | 2.34 |
| Glycerin | 4.70 |
| Poly(vinylpyrrolidone) | 0.34 |
| Sodium bicarbonate | 20.75 |
| Citric acid | 36.75 |

This can be used in pharmaceutical, osmotic, effervescent devices, and different steroids, antibiotics and other drugs may be dispensed in this manner. The device is manufactured according to the procedure of Example 1. In the environment of use, the device produces a large quantity of foam to carry the agent through the osmotic passageway from the device.

EXAMPLE 4

An osmotic device containing a hematinic agent that is delivered by foam volume displacement is prepared as follows: first, 16 parts by weight of citric acid is moistened and added to 21 parts by weight of sodium bicarbonate with partial fusion occuring and granules formed by kneading them together in a suitable mixer. Next, 20 parts of ferrous fumarate, 10 parts of a urea betaine mixture in a proportion by weight of 5:3, 1 part tartaric acid, 5 parts of sodium chloride, 4 parts of sorbitan monolaurate and 13 parts of sorbitan polyoxyethylene monolaurate are blended and added to the granules with constant mixing with the mixture dried in an oven at 70° to 75° C. Next, the mixture is pressed into tablets and each tablet is surrounded with a semipermeable cellulose acetate membrane and an osmotic passageway is drilled in the membrane. The device may optionally contain an antioxidant to prevent ferric salt formation. The hematinic is dispensed by foam volume displacement when the device is placed in the environment of use.

EXAMPLE 5

An oral, osmotic therapeutic device comprising, in combination, an effervescent analgesic and an antacid prepared according to the procedure of Example 1 is illustrated by the following composition: acetylsalicyclic acid 32.4 mg; sodium bicarbonate 190.4 mg; and citric acid 100.0 mg; which composition on dissolving in aqueous fluid imbibed into the device is osmotically administered as follows: acetylsalicylic acid 32.4 mg; sodium 52.1 mg; citrate 98.5 mg; and, bicarbonate 33.7 mg.

EXAMPLE 6

An oral, osmotic therapeutic device comprising an effective amount of an effervescent antacid prepared according to the procedures set forth in Examples 1 and 5 is illustrated by the following composition: sodium bicarbonate 100.8 mg; citric acid 80.0 mg; and, potassium bicarbonate 30.0 mg; which composition when dissolved in aqueous fluid imbibed into the device is osmotically administered as follows: sodium 27.6 mg;

citrate 78.8 mg; potassium 11.7 mg; and, bicarbonate 12.3 mg.

EXAMPLE 7

An oral, osmotic device, prepared according to the procedures described above, is illustrated by devices containing effervescent compositions comprised as follows: (a) at least one of a member selected from the group consisting of 100 to 1500 mg of potassium bicarbonate, 100 to 1500 mg of sodium bicarbonate, 10 to 750 mg of calcium carbonate and 50 to 500 mg of magnesium carbonate and mixtures thereof, blended with (b) at least one of a member selected from the group consisting of 500 to 1500 mg of citric acid and 500 to 1500 mg of glycine and mixtures thereof. The composition also can contain (c) at least one of a member selected from the group consisting of 25 to 175 mg of magnesium oxide, 50 to 750 mg of magnesium trisilicate, and 50 to 750 mg of dihydroxyaluminum aminoacetate and mixtures thereof, with (c) formulated with at least one member from both (a) and (b). The oral device is useful for both the prescribed and self-medication of gastrointestinal disorders including neutralizing excessive acidity.

The device of this invention uses a unique means for dispensing of numerous agents. While there has been described and pointed out the novel features of the invention as applied to preferred embodiments, those skilled in the art will appreciate that various modifications, changes and omissions in the devices illustrated and described can be made without departing from the spirit of the invention.

What is claimed is:

1. An osmotic device for the continuous dispensing of an active agent to an environment of use, said device comprising:
   a. a shaped wall formed of a semipermeable material that maintains its integrity during the dispensing period and which wall is characterized as permeable to the passage of an external fluid in the environment of use and substantially impermeable to the passage of agent;
   b. the wall surrounding and forming a compartment containing an active agent and an effervescent couple which couple is soluble in the external fluid and which couple exhibits an osmotic pressure gradient across the wall against the external fluid;
   c. a passageway in the wall communicating with the compartment and the exterior of the device for dispensing agent from the device; and
   d. wherein in operation with the device in the environment of use, external fluid is continuously imbibed through the wall into the compartment in a tendency towards osmotic equilibrium at a rate determined by the permeability of the wall and the osmotic pressure gradient across the wall, thereby wetting the couple which reactively produces an effervescent solution which dispenses agent through the passageway from the device at a controlled rate over a prolonged period of time.

2. An osmotic device according to claim 1 wherein the effervescent couple comprises an acidic component and a basic component which when brought into fluid reactive contact effervesces.

3. An osmotic device according to claim 1 wherein the active agent contains potassium for use in potassium replacement therapy.

4. An osmotic device according to claim 1 wherein the effervescent couple contains a member selected from the group of pharmaceutically acceptable acids consisting of malic, fumaric, tartaric, itaconic, maleic, citric, adipic, succinic, mesaconic, glycine and mixtures thereof.

5. An osmotic device according to claim 1 wherein the effervescent couple contains a member selected from the group consisting of sodium carbonate, potassium carbonate, calcium carbonate, magnesium carbonate, sodium bicarbonate, potassium bicarbonate, magnesium bicarbonate, calcium bicarbonate, and mixtures thereof.

6. An osmotic device according to claim 1 wherein the agent is acetylasalicylic acid and the couple consists of sodium bicarbonate and citric acid.

7. An osmotic device according to claim 1 wherein the compartment contains sodium bicarbonate, potassium bicarbonate and citric acid.

8. An osmotic device according to claim 1 wherein the compartment contains a composition comprising potassium bicarbonate, potassium chloride, citric acid and a carbohydrate.

9. An osmotic device according to claim 1 wherein the compartment contains citric acid, sodium bicarbonate and a ferrous compound.

10. An osmotic device according to claim 1, wherein the active agent is a member selected from the group consisting of acetazolamide, dichlorophenamide quinidine, norethindrone, norethynordrel, diazepam, norethynodrel with ethynylestradiol 3-methyl ether, metazolamide, pentaerythritol tetranitrate, salicylamide, ascorbic acid, calcium lactate, salicyclic acid, sodium salicylate, choline salicylate, acetaminophen and phenacetin.

11. An osmotic device for the continuous dispensing of an active agent to an environment of use, said device comprising:
   a. a shaped wall formed of a semipermeable material that maintains its integrity during the dispensing period and is characterized as permeable to the passage of an external fluid in the envornment of use and substantially impermeable to the passage of agent;
   b. the wall surrounding and forming a compartment containing an active agent characterized by having limited solubility in the external fluid and exhibiting a limited osmotic pressure gradient across the wall against the fluid;
   c. an effervescent couple that is soluble in the fluid and which couple exhibits an osmotic pressure gradient across the wall against the fluid present in the compartment;
   d. a passageway in the wall for dispensing agent from the device, said passageway structured and adapted for dispensing an effervescent solution from the device, and;
   e. wherein in operation with the device in the envornment of use, external fluid is imbibed through the wall into the compartment in a tendency towards osmotic equilibrium at a rate controlled by the permeability of the wall and the osmotic gradient across the wall, thereby continuously dissolving the couple which reactively effervesces and forms a solution-containing suspended agent that is dispensed through the passageway from the device at a controlled rate of a prolonged period of time.

12. An osmotic device for continuous dispensing of an agent according to claim 11 wherein the compartment additionally contains a surface-active agent.

13. An osmotic device for dispensing an active agent according to claim 11 wherein the compartment contains acetylsalicylic acid, citric acid, sodium bicarbonate and monocalcium phosphate dibasic.

14. An osmotic device for continuously dispensing an active agent to an environment of use, said device comprising:
 a. a shaped wall formed of a semipermeable material that maintains its integrity during the dispensing period, is permeable to the passage of an external fluid in the environment of use and substantially impermeable to the passage of agent;
 b. the wall surrounding and forming a compartment containing an active agent having limited solubility in the external fluid, and a foam-forming agent;
 c. an effervescent couple present in the compartment, which couple is soluble in the fluid, exhibits an osmotic pressure gradient across the wall against the fluid and is capable of evolving gaseous carbon dioxide;
 d. a passageway in the wall structured and adapted for dispensing foam from the device; and,
 e. wherein in operation with the device in the environment of use, external fluid is imbibed through the wall into the compartment causing the couple to evolve carbon dioxide which in the presence of fluid and the foam-forming agent produces foam that dispenses active agent through the passageway from the osmotic device at a controlled rate over a prolonged period of time.

15. An osmotic device according to claim 14, wherein the couple is comprised of a member selected from the group consisting of an inorganic and organic acid, and a compound capable of evolving carbon dioxide in the presence of fluid and the acid and which compound is selected from the group consisting of pharmaceutically acceptable alkali metal carbonates, alkali metal bicarbonates, alkaline earth carbonates, alkaline earth bicarbonates and mixtures thereof.

16. An osmotic device according to claim 15 wherein the active agents are mixed with a surfactant.

17. An oral osmotic device for dispensing an active agent, said device comprising:
 a. a wall formed of a semipermeable material that maintains its integrity during the dispensing period, is permeable to the passage of external fluid present in the gastrointestinal tract and is substantially impermeable to the passage of agent, the wall surrounding:
 b. a compartment containing the agent comprised of at least one member selected from the group consisting of 100 to 1500 mg of potassium bicarbonate, 100 to 1500 mg of sodium bicarbonate, 10 to 750 mg of calcium carbonate and 50 to 100 mg of magnesium carbonate and mixtures thereof, blended with at least one member selected from the group consisting of 50 to 1500 mg of citric acid and 500 to 1500 mg of glycine and mixtures thereof,
 c. a passageway in the wall adapted and sized for dispensing the agent from the device; and
 d. wherein in operation with the device in the environment of use, external fluid is imbibed through the wall into the compartment at a controlled rate causing the agent to effervesce and be dispensed through the passageway from the device.

18. An oral osmotic device according to claim 17 wherein the agent is also blended with at least one member selected from the group consisting of 25 to 175 mg of magnesium oxide, 50 to 750 mg of magnesium trisilicate and 50 to 750 mg of dihydroxyaluminum aminoacetate and mixtures thereof.

19. An oral osmotic device according to claim 17 wherein the device is used for neutralizing excessive acidity in the gastrointestinal tract.

20. An oral osmotic device according to claim 16 wherein the device contains an an orally administrable pharmaceutically acceptable analgesic selected from the group consisting of acetylsalicylic acid, salicylic acid, sodium salicylate, choline salicylate, cetaminophen and phenacetin and mixtures thereof.

21. An osmotic device for continuously dispensing an active agent to an environment of use, said device comprising:
 a. a shaped wall formed of a semipermeable material that maintains its integrity during the dispensing period, is permeable to the passage of an external fluid in the environment of use and is substantially impermeable to the passage of agent, the wall surrounding and defining:
 b. a compartment containing (1) an active agent, (2) an effervescent composition which composition reactively effervesces in the presence of fluid in the compartment, and (3) an osmotically-effective compound which compound is soluble in the external fluid and also exhibits an osmotic pressure gradient across the wall against the fluid;
 c. a passageway in the wall structured and adapted for dispensing an agent from the device; and,
 d. wherein in operation with the device in the environment of use, external fluid from the environment is imbibed through the wall into the compartment in a tendency towards osmotic equilibrium at a rate determined by the permeability of the wall and the osmotic pressure gradient across the wall thereby causing the composition to effervesce and dispense the active agent through the passageway at a controlled rate from the device.

22. An osmotic device according to claim 21 wherein the compartment contains a foam-forming agent.

23. An osmotic device according to claim 21 wherein the compartment contains a surfactant.

24. A method for continuously administering an active agent having limited solubility in gastrointestinal fluid to the gastrointestinal tract of a warm blooded animal comprising:
 a. admitting into the gastrointestinal tract an osmotic device comprising;
  1. a shaped wall formed of a semipermeable material that is permeable to the passage of gastrointestinal fluid and is substantially impermeable to active agent;
  2. the wall surrounding and forming a compartment containing the active agent, a foam-forming agent, and an effervescent couple which couple is soluble in fluid that enters the compartment and which couple exhibits an osmotic pressure gradient across the wall against the fluid;
  3. a passageway in the wall for administering agent from the device;
 b. dissolving said couple in the compartment in the gastrointestinal fluid being imbibed through the wall into the compartment at a rate determined by the permeability of the wall and the osmotic pressure gradient across the wall to continuously dissolve the couple and produce an effervescent solution which reacts with the foam-forming agent to produce foam that mixes with the active agent; and, c. administering the active agent from the device at a controlled and continuous rate by foam-transporting the agent through the passageway to the gastrointestinal tract over a prolonged period of time.

* * * * *